(12) United States Patent
Towse et al.

(10) Patent No.: US 10,195,004 B2
(45) Date of Patent: Feb. 5, 2019

(54) MULTIPLE LAYER COATING AND COATING METHOD FOR DENTAL DEVICES AND THE LIKE

(71) Applicant: ZEST IP HOLDINGS, LLC, Carlsbad, CA (US)

(72) Inventors: Ross Williams Towse, Fort Wayne, IN (US); Nicholas Knapmeyer, San Marcos, CA (US); Luming Tang, Davis, CA (US)

(73) Assignee: ZEST IP HOLDINGS, LLC, Carlsbad, CA (US)

( * ) Notice: Subject to any disclaimer, the term of this patent is extended or adjusted under 35 U.S.C. 154(b) by 0 days.

(21) Appl. No.: 15/367,016

(22) Filed: Dec. 1, 2016

(65) Prior Publication Data

US 2017/0165039 A1    Jun. 15, 2017

Related U.S. Application Data

(60) Provisional application No. 62/265,014, filed on Dec. 9, 2015.

(51) Int. Cl.
| | |
|---|---|
| *A61C 13/225* | (2006.01) |
| *A61C 13/09* | (2006.01) |
| *A61C 13/00* | (2006.01) |
| *A61C 13/08* | (2006.01) |
| *A61K 6/00* | (2006.01) |
| *A61C 8/00* | (2006.01) |

(52) U.S. Cl.
CPC .......... *A61C 13/09* (2013.01); *A61C 8/0013* (2013.01); *A61C 13/0006* (2013.01); *A61C 13/082* (2013.01); *A61K 6/0017* (2013.01); *A61K 6/0023* (2013.01); *A61K 6/0026* (2013.01); *A61K 6/0044* (2013.01); *A61C 8/005* (2013.01)

(58) Field of Classification Search
CPC .......... A61C 8/00; A61C 13/225; A61L 27/30
See application file for complete search history.

(56) References Cited

U.S. PATENT DOCUMENTS

| | | |
|---|---|---|
| 5,116,694 A | 5/1992 | Tsukada et al. |
| 7,587,919 B1 | 9/2009 | Young |

(Continued)

OTHER PUBLICATIONS

International Search Report and Written Opinion of International Patent Application No. PCT/US2016/064483 dated Mar. 13, 2017 from the International Search Authority, Korean Intellectual Property Office.

(Continued)

*Primary Examiner* — Ralph Lewis
(74) *Attorney, Agent, or Firm* — Procopio; Noel C. Gillespie

(57) ABSTRACT

A multi-layer coating of alternating titanium nitride (TiN) and titanium carbo nitride (TiCN) layers is applied to at least part of a dental device for use in attaching crowns, overdentures, and the like in a patient's jaw, where the outermost layer is TiCN with a predetermined percentage of carbon to produce a pink color. The pink outermost layer is of sufficient thickness to conceal the color of the underlying layers, and is very hard and resistant to wear and damage in use. At the same time, the outermost TiCN layer is of a color consistent with the gingival anatomy, and is very hard and resistant to wear and damage in use.

19 Claims, 2 Drawing Sheets

(56) References Cited

U.S. PATENT DOCUMENTS

| | | | | |
|---|---|---|---|---|
| 2009/0155559 | A1* | 6/2009 | Xu | C23C 30/005 |
| | | | | 428/216 |
| 2010/0129626 | A1* | 5/2010 | Langhorn | C23C 16/0272 |
| | | | | 428/216 |
| 2012/0035739 | A1 | 2/2012 | Wilhemsson et al. | |

OTHER PUBLICATIONS

Antunes et al, Study of the corrosion resistance and in vitro biocompatibility of PVD TiCN-coated AISI 316 L austenitic stainless steel for orthopedic applications, Surface & Coatings Technology 205, 2010, pp. 2074-2081.

Serro et al, A comparative study of titanium nitrides, TiN, TiNbN and TiCN, as coatings for biomedical applications, Surface & Coatings Technology 203, 2009, pp. 3701-3707.

\* cited by examiner

MULTIPLE LAYER COATING AND COATING METHOD FOR DENTAL DEVICES AND THE LIKE

CROSS-REFERENCE TO RELATED APPLICATIONS

This application claims the benefit of Provisional App. No. 62/265,014 filed on Dec. 9, 2015, and the contents of the aforementioned application are incorporated herein by reference in their entirety.

BACKGROUND

1. Field of the Invention

This invention relates generally to multiple layer coatings and coating methods for hard metal or metal alloy substrates, and is particularly concerned with such coatings and methods for application to dental devices such as abutments or bars for attachment of dentures, partial dentures, crowns and the like to implants and tooth roots, or for application to surfaces of dental implants such as transgingival or bone level implants and the like.

2. Related Art

Dental devices such as implants for attachment to an existing tooth root, abutments for releasable or fixed attachment of partial or full denture devices to implants or tooth roots, single tooth abutments for attachment to crowns, transgingival implants for patients with bone loss, and implant bars are typically made from biocompatible metals such as pure titanium, titanium alloy, stainless steel or cobalt chrome. Such materials are susceptible to damage and wear, particularly in the case of abutments for removable attachment to an overdenture or the like which is repeatedly removed by the patient or the dentist for cleaning or replacement. Such dental devices are often coated with a layer of titanium nitride which is harder than the metal of the device itself, but this material is also brittle and can flake off with time. Another issue is appearance. The metal tooth abutment for attachment of a crown can appear between the gum line and crown over time, and also is darker than the crown material and can often be seen through the gum, above the gum, or through the crown. The same applies to transgingival implants which can extend one to two mm above the bone level and be visible through the gum or above the gum. Such implants are sometimes coated with a pink layer of material for aesthetic reasons, but this layer becomes damaged over time with repeated cleanings and the like.

SUMMARY

According to one aspect, a dental device for use in attaching crowns, overdentures, and the like in a patient's jaw comprises a substrate of biocompatible material and a multi-layer coating applied to the substrate by a vapor deposition process, the multi-layer coating comprising one or more inner layers comprising at least an innermost layer of titanium nitride applied to the substrate, and a final, outermost layer of titanium carbo nitride (TiCN) applied to an underlying inner layer and having a predetermined composition of carbon, nitrogen and titanium to produce a durable pink color. The pink outermost layer is of sufficient thickness to conceal the color of the underlying grey or darker layers. At the same time, the outermost TiCN layer is of a color consistent with gingival anatomy, and is very hard and resistant to wear and damage in use.

A durable pink color similar to gum color is desirable in dental implants, bars, abutments and other metal dental attachment devices since it is more aesthetically pleasing and less likely to stand out and be obvious to others when the patient is talking, eating, or smiling.

In some aspects, the multi-layer coating comprises three, four or more layers of alternating titanium nitride (TiN) and titanium carbo nitride TiCN. In one variation, six layers are provided, with a graded transition between each layer and the next. In one variation, the percentage of carbon in successive TiCN layers increases from the innermost TiCN layer to the outermost, "pink" TiCN layer. In some aspects, at least some of the layers are of varying thickness.

According to another aspect, a method of applying a coating to a dental appliance or device used in a dental attachment system is provided, which comprises applying a series of successive layers to a surface of the dental appliance using a physical vapor deposition process (PVD) process, the layers comprising at least an inner layer of titanium nitride (TiN) and an outer layer of titanium carbo nitride (TiCN) having a predetermined percentage of carbon sufficient to produce a pink color. In one variation, the layers include at least a second inner layer of TiCN applied to the inner layer, and a third inner layer of pure TiN applied to the second inner layer, where the percentage of carbon in the second inner layer is less that the percentage of carbon in the outer layer. In another variation, a total of six layers are applied, comprising the first to third inner layers, a fourth inner layer of TiCN applied to the third inner layer of TiN, and a fifth inner layer of pure TiN applied to the fourth inner layer, with the outer layer of TiCN applied to the fifth inner layer. In one aspect, the TiCN layers are applied using a mixture of nitrogen and carbon containing gases, and the percentage of carbon containing gas in the mixture is gradually increased from zero to a selected percentage between each TiN layer and successive TiCN layer over a selected time period until a steady state is reached for the TiCN layer, and the percentage of carbon containing gas is gradually decreased between each TiCN and successive pure TiN layer until the carbon amount is zero. This produces a gradual transition between each different material layer which holds the multiple layers together more strongly. The amount of carbon in each TiCN layer increases from the innermost TiCN layer to the outermost TiCN layer, which may contain up to 30% carbon.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawing, in which like reference numerals refer to like parts, and in which.

DETAILED DESCRIPTION

Certain embodiments as disclosed herein provide for a dental device or appliance with a multi-layer coating and a method of applying the coating to a surface of a dental appliance such as a single tooth or multiple tooth dental abutment, dental implant, abutment bar, or the like.

After reading this description it will become apparent to one skilled in the art how to implement the invention in various alternative embodiments and alternative applications. However, although various embodiments of the present invention will be described herein, it is understood that these embodiments are presented by way of example only, and not limitation.

Figure 1:
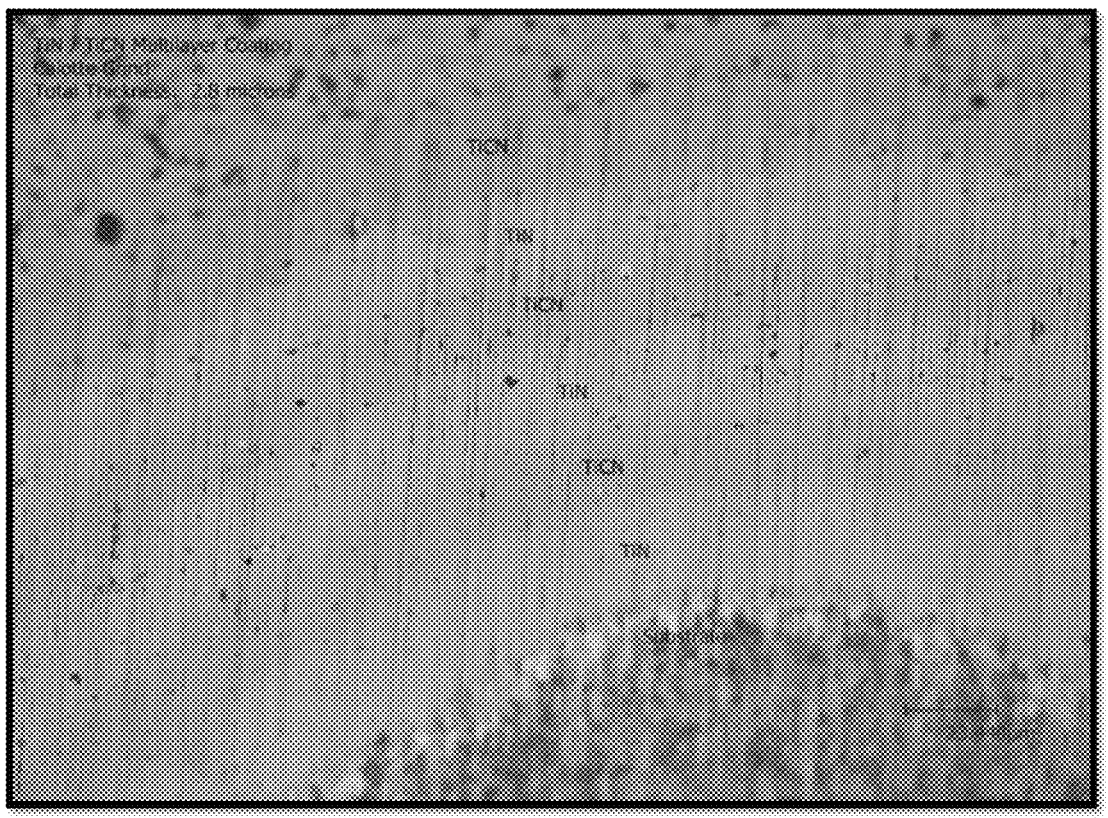
FIG. 1 is a photograph showing an enlarged calotte grind cross section through part of one embodiment of a dental appliance substrate with a multiple layer coating applied to the substrate.
Figure 2:
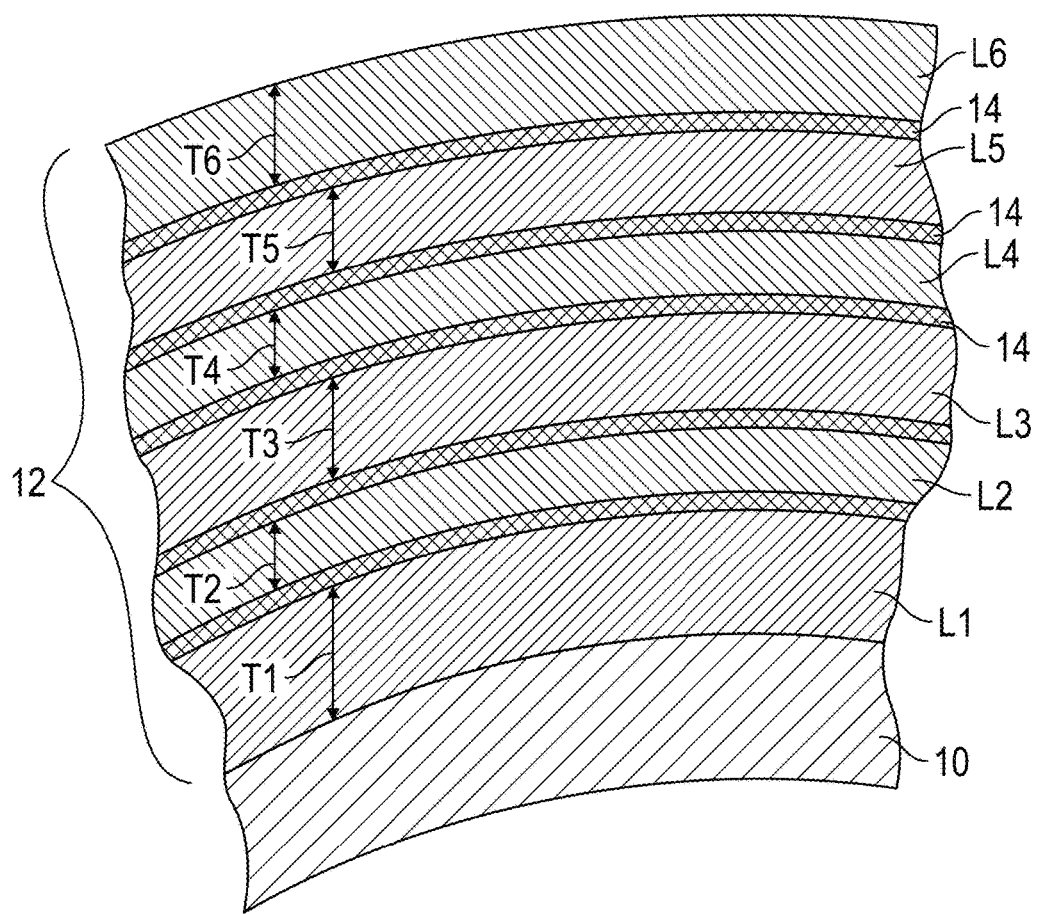
FIG. 2 is a simplified cross-sectional drawing on an enlarged scale illustrating the layers of the embodiment of FIG. 1 in more detail.

FIGS. 1 and 2 are cut-away views of part of a multi-layer coating of one embodiment applied to a substrate 10. Multi-layer coating 12 has alternating layers of titanium nitride (TiN) and titanium carbo nitride (TiCN). FIG. 1 is a calotte grind (ball—radial grind) of the coating demonstrating the presence of six distinct coating layers and lack of porosity in the surface. This embodiment was made using the method described in more detail below as Example 1. FIG. 2 is a simplified, schematic view of the six layers of FIG. 1 (layers L1 to L6). As seen in FIG. 1, there is a gradual transition, not an abrupt transition, between each layer and the next, as described in more detail below. This gradual transition is represented simply by the double line 14 between adjacent layers in the schematic view of FIG. 2.

In some embodiments, the multi-layer coating is applied over part or all of the outer surface of a dental appliance such as an implant, abutment, or overdenture bar, but the coated part may be a medical implant or other component in other variations. In some aspects, the dental appliance may be made of biocompatible materials suitable for dental use such as titanium alloy including Ti-6AL-4V ELI, pure titanium, stainless steel, cobalt chromium alloy, or the like. The coating may be used to coat dental appliances such as single tooth cement and screw retained abutments, overdenture abutments for attachment to dental implants or tooth roots, dental implants, and bars. In one example, the appliances may be implants, bars and abutments as manufactured by Zest Anchors of Escondido, Calif., such as Zest Anchors abutments, implants, and other dental attachment parts. The coating may cover the entire outer surface or only part of the outer surface of the part, dependent on the location in the patient's mouth. For example, the coating may be applied to the entire outer surface of a Zest Anchors LOCATOR® abutment, or the coating may be applied to the coronal end of a bone level abutment or to the transgingival section of a transgingival implant.

Although there are six alternating layers of TiN and TiCN in the illustrated coating of FIG. 1, there may be a greater or a lesser number of layers in some variations. As illustrated in FIG. 2, the layers are of varying thickness, starting with an innermost layer L1 of titanium nitride having a first thickness T1, a second layer L2 of titanium carbo nitride having a thickness T2, a third layer L3 of titanium nitride having a thickness T3, a fourth layer L4 of titanium carbo nitride having a thickness T4, a fifth layer L5 of titanium nitride having a thickness T5, and a sixth or outer layer L6 of titanium carbo nitride having a thickness T6. The amount of carbon in layers L2, L4 and L6 varies from the lowest percentage of carbon in layer L2 and the highest percentage or ratio of carbon in outermost layer L6. The percentage or ratio of carbon in outermost layer L6 is selected so that the outermost layer has a light pink color or coloration desirable for a dental application and is of sufficient thickness to be opaque, so that the color of the underlying layer cannot be seen. This means that any exposed part of an abutment or exposed transgingival portion of an implant blends in at least substantially with the surrounding pink gum tissue and provides a more aesthetically pleasing appearance.

In one aspect, the coating 12 is directly deposited on substrate 10 using a cathodic arc physical vapor deposition (PVD) process. In one variation of the method which produced the sample illustrated in FIG. 1, an Eifeler-Vacotec Alpha400P Cathodic Arc Physical Vapor Deposition Machine as made by the Eifeler Group of Dusseldorf, Germany was used, but other PVD machines may be used in some variations. In this vacuum deposition process, titanium atoms are vaporized from commercially pure titanium targets (ASTM F67, Grade 2) by induction of an electrical arc. The ionized titanium atoms are then accelerated onto a biased (negatively charged) device surface, i.e. the surface of the selected dental appliance, where they combine with nitrogen and/or carbon atoms to build up the coating layer. The nitrogen and carbon atoms are introduced to the vacuum chamber directly using ultra high purity gases (UHP 99.999% N2 and UHP 99.95% CH4). The layers of TiN and/or TiCN are deposited for a predetermined period of amp-hours to form a well adhered, non-porous, thin film surface with a total coating thickness of approximately 3 microns in some embodiments, although the coating thickness may be larger or smaller in some variations.

In one aspect, the substrate is titanium alloy (conforming to ASTM F136) and the coating chemistry is composed of Ti, N, and C atoms generated from Grade 2 titanium (ASTM F67) and ultra-high purity process gases (N2 and CH4). There are no other materials present in the coating. Other substrate materials may be used in some variations.

The type and composition of the layer formed is determined by the process gas or process gas combinations introduced to the vacuum when the electrical arc is induced on the titanium targets. If no gases are introduced to the vacuum, pure titanium is sputtered onto the surface. If nitrogen (N2) gas is introduced to the vacuum, titanium nitride (TiN) is formed on the surface. If nitrogen (N2) and methane (CH4) are introduced simultaneously, a lattice of titanium carbo nitride (TiCN) is formed on the surface.

TiN and TiCN coatings all form a tightly packed face centered cubic molecular structure, and are well known to be functionally non-porous. The ratio of the nitrogen to methane gas in the chamber controls to percentage of carbon atoms in the lattice and the properties of the coating layers, including color and hardness. Coatings with less carbon have properties similar to TiN (gold color, hard), while coatings with ultra-high carbon content have properties more in line with titanium carbide TiC (dark grey metallic color, extremely hard). Low to moderate carbon-containing coatings have properties in the middle of these extremes (pink or violet color, very hard).

In one aspect, the coating 10 is a high technology coating composed of multiple layers of titanium nitride (TiN) and titanium carbo nitride (TiCN). In alternative embodiments, there may be two, four, or eight or more layers with TiN as the innermost layer and pink-colored TiCN as the outermost layer. The total thickness of the multiple layer coating 10 in one embodiment was approximately 3 microns, and the coating thickness in alternative embodiments may be in the range from 2 to 5 microns. In one aspect, the coating is composed of the following layers generated through varying the percentages of carbon containing gas introduced to the PVD process:

1. Titanium alloy substrate 10.
2. Pure Titanium Nitride (0% carbon)—layer L1
3. Titanium Carbo Nitride (5-10% carbon)—layer L2
4. Pure Titanium Nitride (0% carbon)—layer L3

5. Titanium Carbo Nitride (10-15% carbon)—layer L4
6. Pure Titanium Nitride (0% carbon)—layer L5
7. Titanium Carbo Nitride (15-30% carbon)—layer L6

In the coating method, the amount of carbon in each TiCN layer is graded gradually in until the desired ratio of carbon to nitrogen is reached, and after a predetermined time period of steady state, the amount of carbon in the injected gas mixture is gradually graded out for layer L2 to L3 and layer L4 to L5 into the pure titanium nitride layers L3 and L5. This results in a gradual transition 14 from each layer to the next, making a stronger coating with good adhesion between adjacent layers. The control program for the method controls the ratio of gases methane and nitrogen injected into the vapor deposition chamber and the current on the pure titanium target, while the amp hours for each mixture and the surface area to be coated controls the respective layer thicknesses. The outer, pink-colored TiCN layer is of sufficient thickness that the underlying gray or different color TiN layer is not visible through layer L6. In one variation, the thickness of layer L6 was in the range from 0.5-0.6 microns, and in one example was approximately 0.53 microns.

The coating is layered in this manner to increase the toughness of the coating, which is a function of its ductility, adhesion, and wear properties. The final coating layer of TiCN provides the functional micro-hardness (>3000 HV) and the "pink" coloration desired for dental application.

Pure titanium, titanium alloy and titanium nitride are known to be biocompatible for dental applications. The titanium carbo nitride layers are chemically related to titanium nitride with a replacement of a percentage of carbon atoms for nitrogen in the lattice. As both titanium nitride and full carbon coatings, such as diamond like carbon (DLC), are well known to have acceptable biocompatibility, it would be expected that a TiCN complex would also be biocompatible. Published research on TiCN confirms this to be the case.

As noted above, the alternating layers of TiN and TiCN are of different thicknesses, and in one embodiment the thicknesses of successive layers were in the following approximate ranges: L1 0.55-0.65 microns; L2 0.3-0.4 microns; L3 0.5-0.6 microns; L4 0.3-0.4 microns; L5 0.4-0.5 microns; L6 0.5-0.6 microns. In one exemplary coating, the layer thicknesses were:
L1=TiN=0.59 microns
L2=TiCN1=0.35 microns
L3=TiN=0.53 microns
L4=TiCN2=0.35 microns
L5=TiN=0.45 microns
L6=TiCN3=0.53 microns.

Example 1

The following is one example of a coating method used to produce the coating 12 illustrated in the embodiment of FIG. 1 with the respective layer thicknesses listed above:

The method used an Eifeler-Vacotec Alpha400P Cathodic Arc Physical Vapor Deposition Machine Chamber Volume (without planetary, which takes up volume). The chamber volume was approximately 407 liters (406,875 cm$^3$).

Constant Pressure Mode: 0.012 mbar (vacuum is pulling at all times, 1 atm=1013 mbar), the gas flow rates are variable (but in ratio as necessary) to maintain the vacuum level.
Coating Heater's Temperature: 460 C
Target Amperage: 60 A Layer L1: Titanium Nitride (no carbon in the matrix, 1:1 ratio)
Ti from the targets (90 amp-hours)
Settings: 100% volume N2 (actual from a past run: 730 standard cubic centimeter per minute or sccm).
Layer L2: Titanium carbon nitride (methane gas graded in/out over 1.2 minutes)
Ti from the targets (60 amp-hours)
Settings: 93.5% volume N2, 6.5% by volume CH4 (actuals from a past run: 625 sccm N2 and 40 sccm of CH4).
Layer L3: Titanium Nitride (no carbon in the matrix, 1:1 ratio).
Ti from the targets (90 amp-hours)
Settings: 100% volume N2 (actual from a past run: 725 SCCM)
Layer L4: Titanium carbon nitride (methane gas graded in/out over 2.3 minutes)
Ti from the targets (60 amp-hours)
Settings: 87.7% volume N2, 12.2% by volume CH4 (actuals from a past run: 550 sccm N2 and 75 sccm CH4)
Layer L5: Titanium Nitride (no carbon in the matrix, 1:1 ratio)
Ti from the targets (90 amp-hours)
Settings: 100% volume N2 (actual from a past run: 720 SCCM)
Layer L6: Titanium carbon nitride (methane gas graded in over 5.7 minutes)
Ti from the targets (120 amp-hours)
Settings: 74.6% volume N2, 25.4% by volume CH4 (actuals from a past run: 415 sccm N2 and 140 sccm CH4).

The total thickness of the coating layer in the above example was 2.8 microns, with individual layer thicknesses approximating or equal to those stated above.

The layered coating described above is extremely tough with good ductility, adhesion, and wear properties. The final coating layer of TiCN has a predetermined percentage of carbon to produce the desired pink or substantially gum-like coloration for dental purposes, and is of a desired thickness so that it is opaque and conceals the color of the underlying layers. The pink color is more aesthetically pleasing than the normal gray color of dental appliance materials with or without standard TiN coatings. With this coating, the appearance of abutments or bars when a person removes a removable overdenture for cleaning purposes is more aesthetically pleasing. In the case of single tooth abutments for crowns, any visible part of the abutment at the gum line does not stand out as much since it closely matches the surrounding gum color. If the coating is applied to the apical end of a bone level abutment or to the transgingival section of a transgingival implant, it also helps to conceal the presence of the dental appliance to others through thin gingival tissues or any visible portions above the gingiva and between the crown and gingiva. In the past, these sections of the appliance were traditionally dark or gray and stood out from the surrounding "pink" gum tissue or gingiva.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

We claim:

1. A dental device for use in attaching crowns or overdentures in a patient's jaw, comprising a substrate body of biocompatible material having an outer surface and a multi-layer coating applied to at least part of the outer surface of the substrate, the multi-layer coating comprising:
a plurality of layers comprising:
at least a first, innermost layer of titanium nitride (TiN) applied to at least part of the outer surface of the substrate, and
an outermost layer of titanium carbo nitride (TiCN) having a predetermined composition of carbon, nitrogen and titanium to produce a pink color,
wherein the outermost layer is formed through a deposition process in an environment having a carbon content in a range of at least 15% and no more than 30%.

2. The dental device of claim 1, wherein the multi-layer coating comprises at least four alternating layers of TiN and TiCN.

3. The dental device of claim 2, wherein the outermost TiCN layer contains more carbon than any other layers of TiCN in the coating.

4. The dental device of claim 3, wherein there are six alternating layers of TiN and TiCN, comprising the first, innermost TiN layer, a second layer of TiCN, a third layer of TiN, a fourth layer of TiCN, a fifth layer of TiN, and a sixth layer of TiCN comprising the outermost layer.

5. The dental device of claim 4, wherein the percentage of carbon in the second layer is less than the percentage of carbon in the fourth layer, and the percentage of carbon in the fourth layer is less than the percentage of carbon in the sixth, outermost layer.

6. The dental device of claim 4, wherein a transition layer is located between each adjacent pair of adjacent TiN and TiCN layers, and the percentage of carbon increases from zero to the TiCN layer percentage in respective transition layers between each TiN layer and TiCN layer in a direction towards the outermost layer, and decreases from the TiCN layer percentage to zero in respective transition layers between each TiCN layer and TiN layer in the direction towards the outermost layer.

7. The dental device of claim 2, wherein the outermost layer of TiCN is thicker than any other TiCN layer in the coating.

8. The dental device of claim 1, wherein the thickness of the outermost layer is at least 0.5 microns.

9. The dental device of claim 8, wherein the thickness of the or each other layer of TiCN is in the range from 0.3 to 0.4 microns.

10. The dental device of claim 1, wherein the coating has six alternating layers of TiN and TiCN, the thickness of the outermost layer of TiCN is in the range from 0.5 to 0.6 microns and the thickness of the innermost layer of TiN is in the range from 0.55 to 0.65 microns.

11. The dental device of claim 10, wherein the thickness of each inner layer of TiCN in the coating is in the range from 0.3 to 0.4 microns.

12. The dental device of claim 11, wherein the thickness of each inner layer of TiN between the innermost and outermost layers is greater than the thickness of each inner layer of TiCN and less than the innermost layer of TiN.

13. The dental device of claim 1, wherein the thickness of the coating is in the range from around 2 microns to around 5 microns.

14. A method of applying a coating to a dental appliance used in a dental attachment system, comprising:
applying a series of successive layers to at least part of a surface of a dental appliance, the layers comprising at least an inner layer of titanium nitride (TiN) applied directly to the surface of the dental appliance and an outer layer of titanium carbo nitride (TiCN) having a predetermined percentage of carbon sufficient to produce a pink color,
wherein the outer layer is formed by a deposition process in an environment having a carbon content in a range of at least 15% and no more than 30%.

15. The method of claim 14, wherein the layers are applied by a physical vapor deposition (PVD) process.

16. The method of claim 15, wherein the series of layers comprise at least two additional inner layers comprising a second layer of TiCN applied to the inner layer of TiN and a third layer of pure TiN applied to the second layer of TiCN.

17. The method of claim 16, wherein the series of layers further comprise a fourth layer of TiCN applied the third layer of pure TiN and a fifth layer of TiN applied to the fourth layer of TiCN, the outer layer of TiCN comprising a sixth layer applied to the fifth layer of TiN, where the percentage of carbon in the sixth and outermost layer is greater than the percentage of carbon in any underlying TiCN layers.

18. The method of claim 16, wherein the PVD process includes introducing process gas to the vacuum deposition chamber, and the process gas comprises pure nitrogen gas for each TiN layer of the coating and a mixture of nitrogen and carbon containing gas for each TiCN layer, and the percentage of carbon containing gas for the outermost TiCN layer is higher than the percentage of carbon containing gas used in depositing any other TiCN layer in the coating.

19. The method of claim 18, wherein the PVD process includes gradually increasing the amount of carbon in the gas mixture outwardly from each TiN layer to form a transition layer of gradually increasing carbon content up to the adjacent TiCN layer and gradually decreasing the amount of carbon in the gas mixture outwardly from each TiCN layer to zero carbon at the adjacent TiN layer, whereby a transition layer of gradually increasing carbon content in an outward direction is formed between each TiN layer and the adjacent TiCN layer and a transition layer of gradually decreasing carbon content in an outward direction is formed between each TiCN and the adjacent TiN layer.

* * * * *